US006477418B2

(12) United States Patent
Plicchi et al.

(10) Patent No.: US 6,477,418 B2
(45) Date of Patent: Nov. 5, 2002

(54) IMPLANTABLE HEART STIMULATION SYSTEM WITH AUTOMATIC MODE SWITCHING CONTROLLED BY SYMPATHO-VAGAL BALANCE

(75) Inventors: Gianni Plicchi, Bologna (IT); Bruno Garberoglio, Turin (IT); Guido Gaggini, Milan (IT); Luigi Silvestri, Turin (IT); Laura Vaccarone, Turin (IT); Emanuela Marcelli, Macerata (IT)

(73) Assignee: Sorin Biomedica Cardio CRM S.r.l., Saluggia (IT)

( * ) Notice: Subject to any disclaimer, the term of this patent is extended or adjusted under 35 U.S.C. 154(b) by 0 days.

(21) Appl. No.: 09/903,400

(22) Filed: Jul. 11, 2001

(65) Prior Publication Data

US 2002/0082661 A1 Jun. 27, 2002

(30) Foreign Application Priority Data

Jul. 11, 2000 (EP) .......................... 00114823

(51) Int. Cl.[7] .............................. A61N 1/368
(52) U.S. Cl. ........................................ 607/9
(58) Field of Search ...................... 607/9, 14

(56) References Cited

U.S. PATENT DOCUMENTS

| | | |
|---|---|---|
| 5,144,949 A | 9/1992 | Olson |
| 5,247,930 A | 9/1993 | Begemann et al. |
| 5,531,771 A | 7/1996 | van der Veen |
| 5,549,649 A | 8/1996 | Florio et al. |
| 5,579,200 A | 11/1996 | Rajkanan et al. |
| 5,645,570 A | 7/1997 | Corbucci |
| 5,713,928 A | 2/1998 | Bonnet et al. |
| 5,749,900 A | 5/1998 | Schroeppel et al. |
| 6,226,550 B1 | 5/2001 | Plicchi et al. |
| 6,240,314 B1 | 5/2001 | Plicchi et al. |

OTHER PUBLICATIONS

"Dual-demand pacing for refractory atrioventricular re-entry tachycardia"(Curry et al., PACE, vol. 2 (2), 1979, pp. 137–151).
"Rate Adaptive Cardiac Pacing: Single and Dual Chamber", C.P. Lau, Futura Publishing Company, Inc.; Mount Kisko, NY, 1993—p. 8).
Mode Switching for Atrial Tachyarrhythmias (Sutton et al., American Journal of Cardiology vol. 83, 1999, pp. 202D–210D.

*Primary Examiner*—Scott M. Getzow
(74) *Attorney, Agent, or Firm*—Popovich & Wiles, P.A.

(57) ABSTRACT

An implantable dual-chamber pacemaker system has a means for automatic beat-to-beat adjustment of the maximum allowable variation (MAV) of the sensed atrial rate (AR) as a function of the sympatho-vagal balance, switching from an atrial tracking mode of operation (e.g., DDD or DDD(R)) to a non atrial tracking mode (e.g., VDI or VDI(R)) when either an arrhythmic tachycardic rate, exceeding the MAV, or a sinus tachycardic rate, exceeding the maximum tracking atrial rate (MTAR), is detected. The pacemaker provides logic means for continuously determining the atrial rate variation (ΔAR) and the MAV. The MAV defines the upper limit for the ΔAR above which tracking is not allowed, discriminating between physiological rate variations and arrhythmic variations. The pacemaker system can return to an atrial tracking mode of operation if the AR remains under a defined rate for a defined number of cycles.

22 Claims, 4 Drawing Sheets

Fig_1
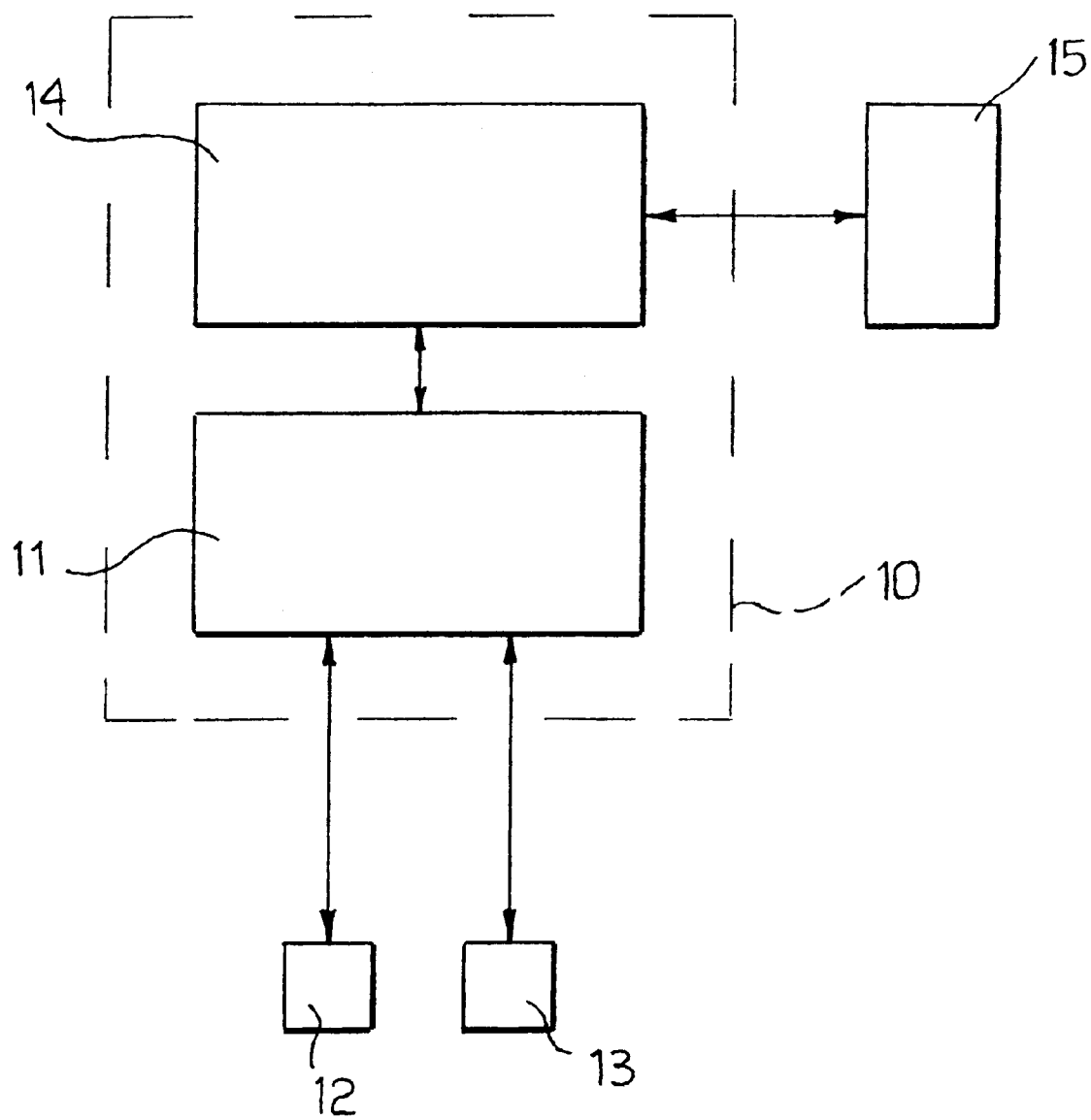

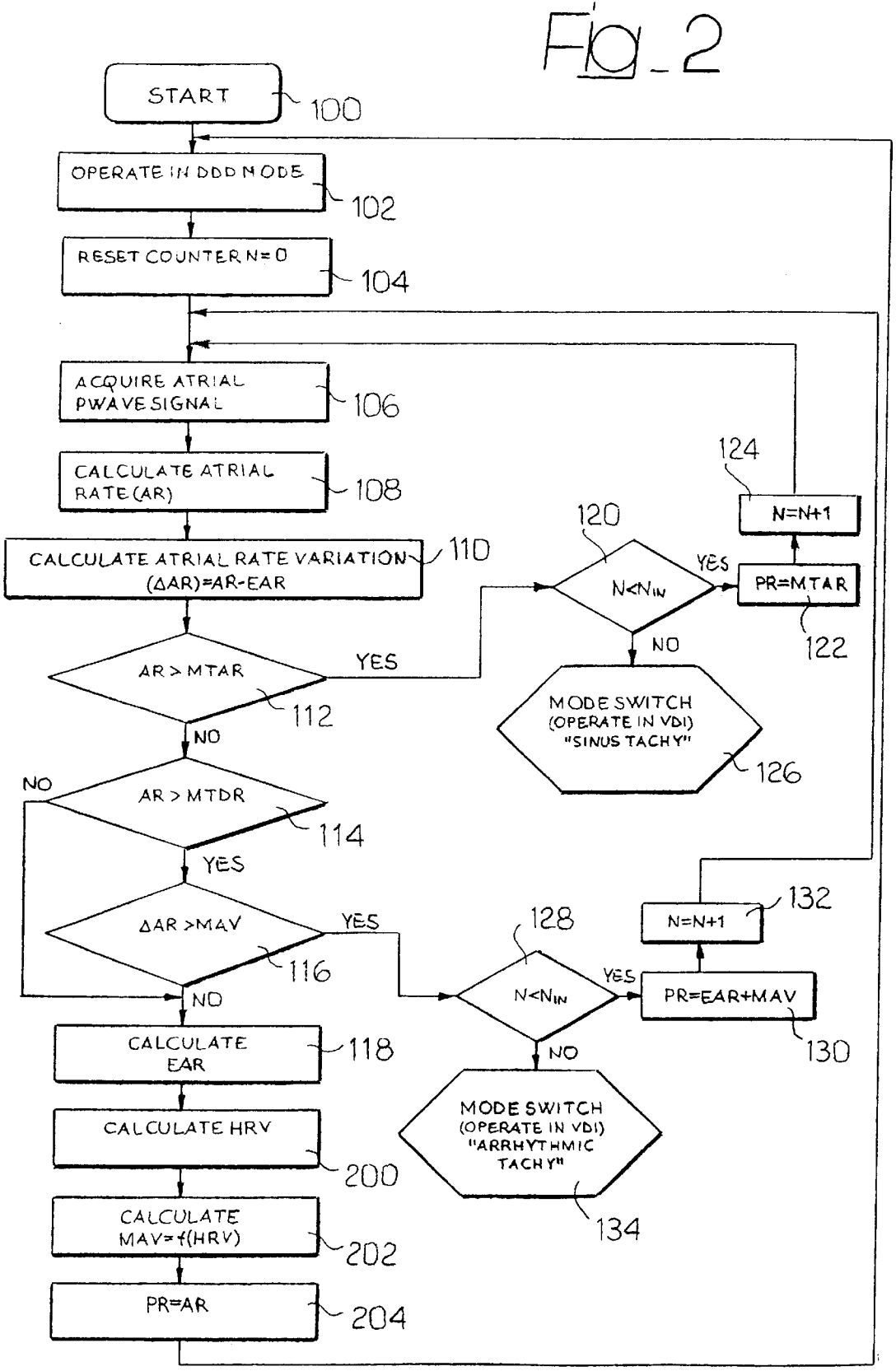
Fig_2

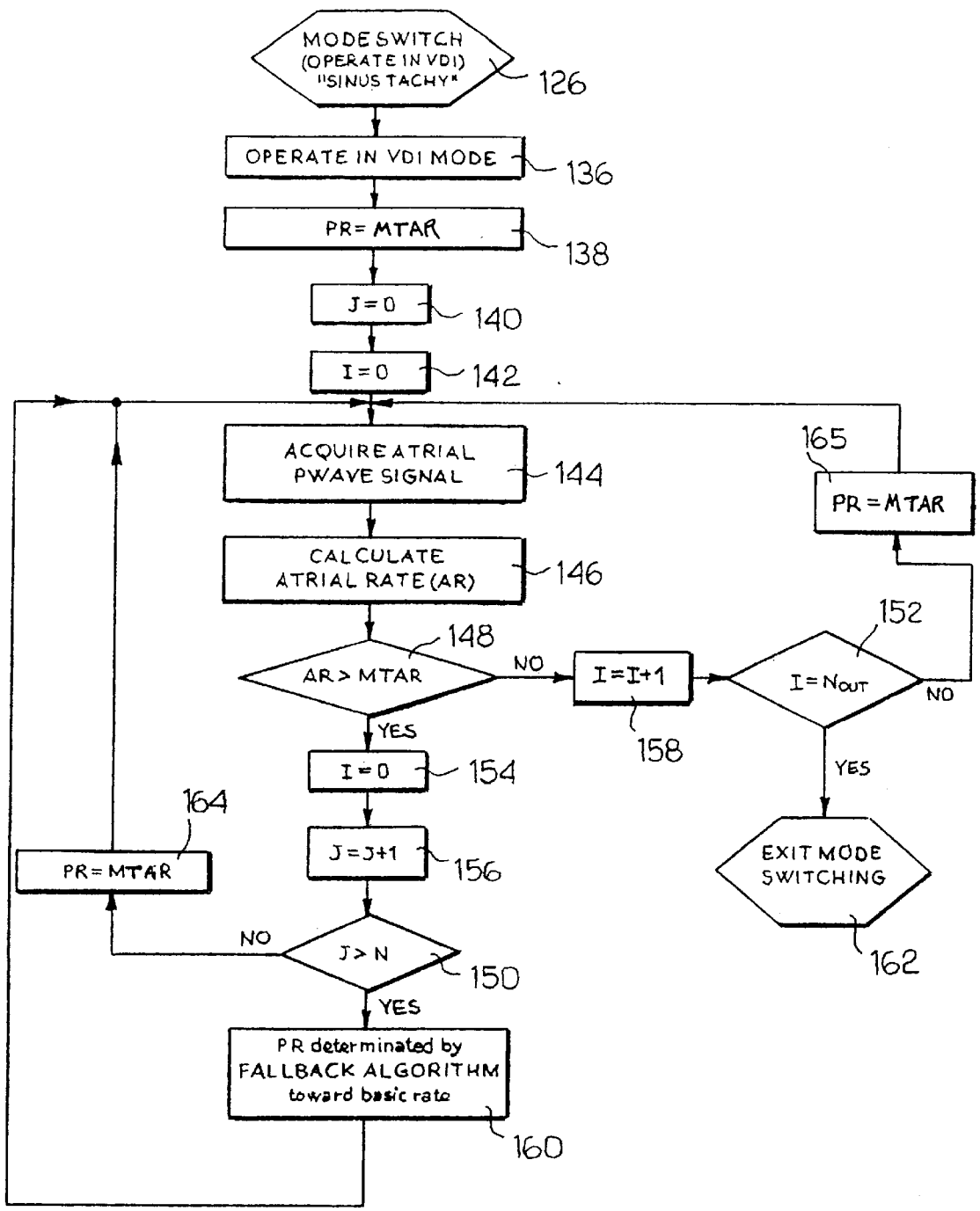
Fig_3

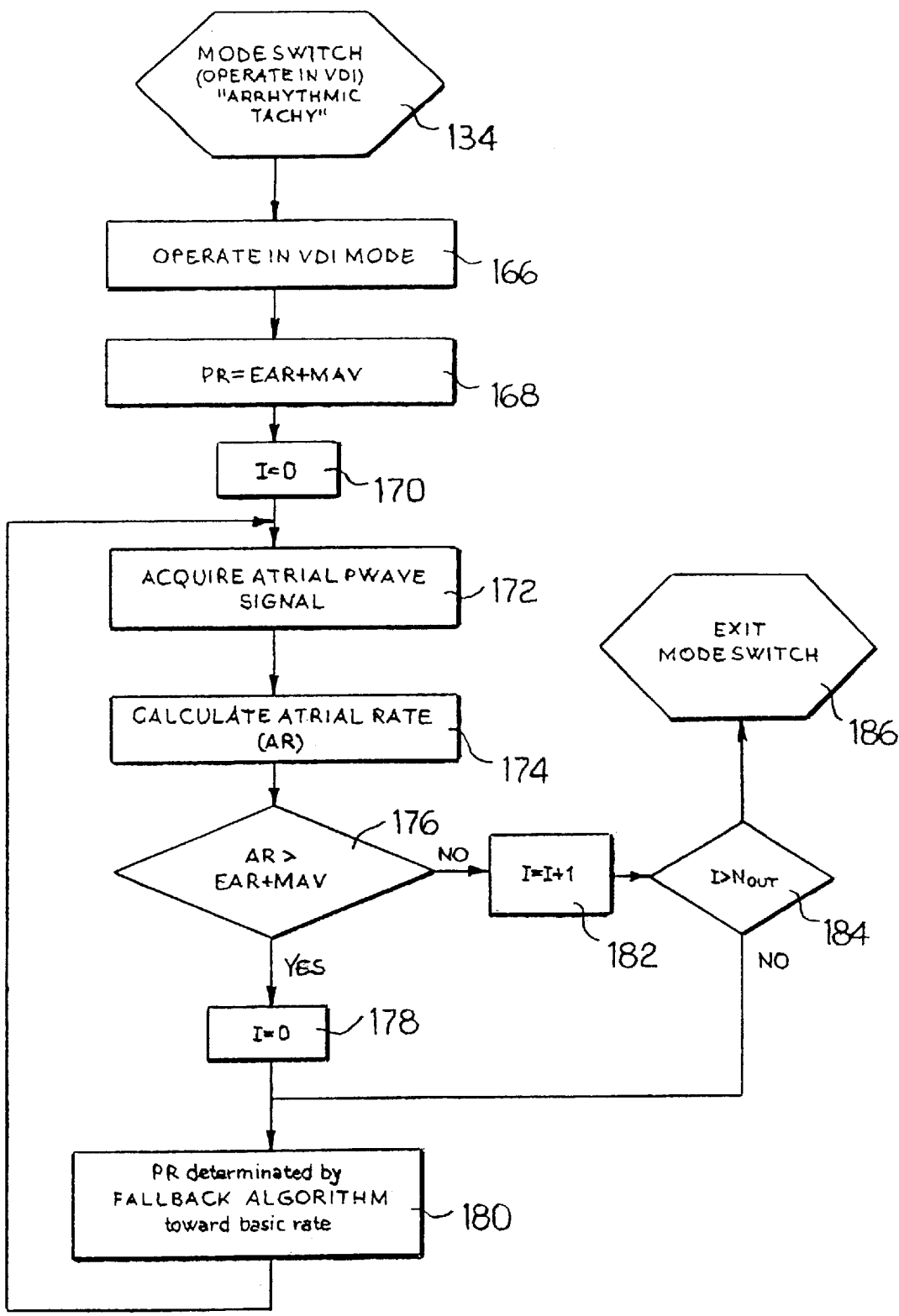
Fig_4

IMPLANTABLE HEART STIMULATION SYSTEM WITH AUTOMATIC MODE SWITCHING CONTROLLED BY SYMPATHO-VAGAL BALANCE

FIELD OF THE INVENTION

The present invention relates to implantable cardiac stimulation devices.

BACKGROUND OF THE INVENTION

It is the function of a pacemaker to provide electrical stimulation pulses to the appropriate chamber(s) of the heart (atria or ventricles) in the event that the heart is unable to beat of its own (i.e., in the event that either the sinoatrial node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when the heart is not beating of its own, as sensed by monitoring the appropriate chamber of the heart for the occurrence of a P-wave or R-wave. If a P-wave or a R-wave is not sensed within a prescribed period of time (which period of time is usually referred to as the "escape interval"), then a stimulation pulse is generated at the end of this prescribed period of time and delivered to the appropriate heart chamber via a pacemaker lead.

Modem pacemakers are generally of two types: i) single chamber pacemakers and ii) dual chamber pacemakers. In a single chamber pacemaker, the pacemaker provides stimulation pulses to, and senses cardiac activity within, a single chamber of the heart (either the right ventricle or the right atrium). In a dual chamber pacemaker, the pacemaker provides stimulation pulses to, and senses cardiac activity within, two chambers of the heart (e.g., both the right atrium and the right ventricle).

One of the most versatile programmable pacemakers available today is the DDDR pacemaker. This pacemaker represents a fully automatic pacemaker, which is capable of sensing and pacing both the atrium and the ventricle, and is also capable of adjusting the pacing rate based on one or more physiological parameters such as minute ventilation, heart contractility, QT interval and/or mechanical parameters such as activity and body acceleration.

Unfortunately, in some instances, a given patient may develop fast atrial rhythms which result from a pathologic arrhythmia such as supraventricular tachycardia, fibrillation or flutter. In these cases, patients who require DDD/DDDR pacing are limited by the potential for rapid ventricular pacing due to tracking of the atrium rhythm.

As these patients require atrioventricular synchrony during periods of sinus rhythm, attempts have been made in the art to prevent undesirable tracking of pathologic atrial arrhythmias by automatically switching the pacemaker's mode of operation from an atrial tracking pacing mode to a non atrial tracking pacing mode.

Thus it would be desirable for the pacemaker to switch the pacing mode from an atrial tracking mode to a non atrial tracking mode only if a pathologic supraventricular arrhythmia is detected, thus avoiding repetitive mode switching based on fluctuations in the sensed atrial rate.

A variety of mode-switch algorithms have been developed to avoid inappropriate tracking of atrial arrhythmias and to provide tracking of the sinus node at all other times. The mode-switch algorithm differs from manufacturer to manufacturer and, at least at present, this is confusingly given different names, e.g., automatic mode-switching (AMS), or Atrial Tracking Response (ATR). Basically, these algorithms enable the pacemaker to change the mode of response to atrial sensed events from a tracking DDD(R) to a non tracking mode (VVI(R) or DDI(R)), when the intrinsic or average atrial rate exceeds a programmed switch rate.

One of the earliest mode switching devices, described in "Dual-demand pacing for refractory atrioventricular re-entry tachycardia" (Curry et al., PACE, Vol.2 (2), 1979, pp.137–151), was designed to pace at a fixed rate of 70 beats per minute, when sensed heart rates were either below this rate or above 150 beats per minute.

Typically, the threshold switch rate at which switching occurs is entered during programming of the pacemaker upon installation and remains fixed thereafter. This mode switching criterion may cause problems for patients who exhibit normal sinus tachycardia due to physical activity or emotional stress. Another difficulty associated with previous techniques is that mode switching occasionally occurred due to a single premature atrial contraction or fluctuations of atrial rhythm.

In the above instances, rates slightly exceeding the programmed switch rate are not indicative of a supraventricular arrhythmia. These patients may thus be subjected to undesirably frequent mode switching occurrences as their atrial rates slightly exceed and then drop below the programmed switch rate.

Consequently, algorithms have been developed for switching pacing modes which have the capability of determining an atrial rate representative of the actual atrial activity to enhance the chances of a correct detection of an atrial arrhythmia, thus avoiding a response based on a single premature atrial contraction or fluctuations of atrial rhythm above the programmed switch rate.

In U.S. Pat. No. 5,144,949, a dual chamber pacemaker is described with automatic mode switching between the DDD mode, the VVIR mode and DDDIR mode, based on the difference between the average sensor rate and the average atrial rate; whenever the sensor rate and the atrial rate are too different and the difference exceeds a programmable function of the two rates, the mode is switched to VVIR to avoid tracking high atrial rates.

In U.S. Pat. No. 5,549,649, a pacemaker is disclosed using a filtered atrial rate (FAR) as a basis for mode switching in order to reduce mode switching responses due, for example, to a single premature atrial contraction or fluctuations in the atrial activity. The FAR is obtained using a rate smoothing filter, which during each cycle limits the amount by which the FAR may change from cycle to cycle. This is accomplished by increasing the FAR by a programmable high rate factor when the intrinsic atrial rate increases, and by decreasing the FAR by a programmable low rate factor when the intrinsic atrial rate decreases.

The optimal use of mode switching was however found to be enhanced by allowing some variability in the programmed threshold mode switch rate on the basis of either new algorithms or measured values of sensed parameters. For these reasons, it is sometimes desired to provide pacemakers that can be programmed with a mode switching threshold rate calculating algorithm.

For example, U.S. Pat. No. 5,579,200 describes an algorithm for calculating the mode switch threshold rate as a function of the programmed base pacing rate. Because the base rate is typically a non-linear function of activity level, the threshold switching rate is also non linear and dependent on the activity level. The threshold switching rate can be equal to the base pacing rate plus a constant or can be some other, more complex function of the base pacing rate and/or activity level.

U.S. Pat. No. 5,713,928 discloses an algorithm to detect atrial arrhythmias, using a first window of atrial acceleration detection, whose duration is a function of the preceding atrial rhythm, for determined rapid atrial rhythm and a second window (Atrial Escape Interval) for a determined slow atrial rhythm, which allows the discrimination between atrial extrasystoles and physiological accelerations of the atrial rhythm.

U.S. Pat. Nos. 5,247,930 and 5,531,771 define a method for determining a so-called physiological rate, as a function of sensed atrial rate, and means for defining a range of atrial rates, the so-called physiological band, relative to and varying with the physiological rate.

As described in "Mode Switching for Atrial Tachyarrhythmias" (Sutton et al., American Journal of Cardiology Vol. 83, 1999, pp. 202D–210D), such mode switching features have been implemented in the pacemakers sold under the trade names Diamond II DDDR, Ruby II DDD and Saphir II VDDR by Vitatron Medical B. V., K I Dierén, the Netherlands.

In such devices the so-called physiological rate is a moving average of the intrinsic atrial rate while the physiological band is a fixed area of 15 beats/min higher and lower than the physiological rate, if mode switching is selected as automatic. Any atrial event outside this band is deemed pathologic and on a beat-to-beat basis a single premature atrial beat that occurs above the physiological band will not be tracked and the flywheel rate or the sensor rate determines the ventricular rate.

From the above, it is evident that the previously described automatic mode switching algorithms based on a programmable or sensor determined upper rate limits and the most recent pacing systems providing means for defining ranges of acceptable atrial rates are lacking in the capability of estimating the physiological processes that regulate the arrhythmogenesis and more specifically the control exerted by the Autonomic Nervous System (ANS).

Furthermore, another limitation of the previous described methods is represented by the inability to detect and control the breathing arrhythmias that arise as rapid variations of the sinus atrial rate; these arrhythmias could either be confused with the onset of a cardiac arrhythmia causing the activation of the mode switching or could be not considered if the range of the acceptable atrial rates is increased with the risk of a lack of sensitivity to possible cardiac arrhythmias.

Most clinicians agree that the balance of the sympathetic autonomic and parasympathetic autonomic nervous systems regulate, to some extent, the sinoatrial (SA) node and the atrioventricular (AV) node of the heart and, thus, largely influence the control of the heart rate. These two nervous systems operate somewhat reciprocally to effect changes in the heart rate; specifically an increase in heart rate can be associated directly with a momentary dominance of the sympathetic activity over the vagal activity, while a reduction of the heart rate can be associated directly with a momentary dominance of the vagal activity over the sympathetic activity.

In that respect, reference may be had to commonly assigned U.S. Pat. No. 5,645,570, where a method and an implantable device are disclosed to measure sympatho-vagal activity in a continuous manner and with time constants such as to allow the possible piloting of a pharmacological and/or electrical therapeutic action. Also, beat-to-beat fluctuations which occur around a person's mean rate are known as heart rate variability (HRV) and are attributed, in part, to the non linear interaction between the two branches of involuntary nervous system.

SUMMARY OF THE INVENTION

The present invention thus has the object of providing an implantable heart stimulation system that overcomes the disadvantages outlined above. The present invention provides a dual chamber cardiac pacing system capable of switching from an atrial tracking mode of operation to a non-atrial tracking mode in response to the occurrence of an atrial arrhythmia.

Still more particularly, the present invention relates to a dual-chamber cardiac pacing system, comprising means for the automatic beat-to-beat adjustment of the Maximum Allowable Variation (MAV) of the sensed atrial rate as a function of the sympatho-vagal balance of the patient, switching from an atrial tracking mode to a non atrial tracking mode of operation when an atrial arrhythmia is detected.

In the presently preferred embodiment of the invention, an implantable dual-chamber pacemaker system is provided having means for an automatic beat-to-beat adjustment of the Maximum Allowable Variation (MAV) of the sensed atrial rate as a function of the sympatho-vagal balance, switching from an atrial tracking mode of operation (e.g., DDD or DDD(R)) to a non atrial tracking mode (e.g., VDI or VDI(R)) when either an arrhythmic tachycardic rate, exceeding the MAV, or a sinus tachycardic rate, exceeding the maximum tracking atrial rate (MTAR) is detected. Thus the invention is essentially based on the recognition that automatic mode switching systems and algorithms can determine their dynamic decisions of switching from an atrial tracking mode to a non atrial tracking mode in response to variations of the sympatho-vagal balance.

The system of the invention preferably provides logic means for continuously determining the atrial rate variation ($\Delta AR$) and the MAV, whereby the MAV defines the upper limit for $\Delta AR$ above which tracking is not allowed, discriminating between physiological rate variations and arrhythmic variations.

Still preferably, the system of the invention further includes the capability of returning to an atrial tracking mode of operation, when the atrial rate variation ($\Delta AR$) remains under the MAV for a definite number of cycles.

In a preferred embodiment, the sympatho-vagal balance is expressed by a proper index of HRV. Still preferably, that index is the number of atrial intervals, which in a predetermined time interval or number of beats differ from the preceding interval by more than a predetermined quantity. In preferred embodiments, the captioned number of beats is 100, the time interval is one minute and/or the predetermined quantity is 50 milliseconds (ms).

In one aspect, this invention is an implantable heart-stimulation system, comprising a first sensing element configured to sense atrial signals; a second sensing element configured to sense ventricular signals; a pulse generator configured to generate atrial and ventricular stimulating signals; and a control unit configured to determine for each cardiac cycle an atrial rate from the sensed atrial signals, to determine for each cardiac cycle a maximum allowable variation of the atrial rate as a function of sympatho-vagal balance, and to switch from an atrial tracking pacing mode to a non-atrial tracking pacing mode when a variation in the atrial rate between a first cardiac cycle and a second cardiac cycle exceeds the maximum allowable variation.

The sympatho-vagal balance may be expressed by heart rate variability and the heart rate variability may be measured by means of an index. The index may be calculated as the number of atrial intervals, which in a predetermined time interval or number of beats differ from the preceding interval more than a predetermined quantity. The maximum allowable variation of the sensed atrial rate may be a positive linear function of an index of the sympatho-vagal balance. The control unit may be configured to determine for each cardiac cycle an estimated atrial rate and wherein the control unit is configured to calculate the variation in the atrial rate as the difference between the sensed atrial rate of a present cardiac cycle and the estimated atrial rate of the previous cardiac cycle. The estimated atrial rate may be a moving average rate calculated at each cycle. The control unit may be programmable.

In a second aspect, this invention is a method of controlling the pacing mode of a heart stimulation system implanted in a patient, the system including first and second sensors for sensing atrial and ventricular signals, a pulse generator for generating and providing atrial and ventricular stimulation pulses to the patient's heart and a control unit for controlling the pacing mode of the system, the method comprising determining in the control unit an atrial rate of the patient's heart from the sensed atrial signals; determining in the control unit a maximum allowable variation of the atrial rate for each cardiac cycle as a function of sympatho-vagal balance; and switching from an atrial tracking pacing mode to a non-atrial tracking pacing mode when a variation in atrial rate from a first cardiac cycle to a second cardiac cycle exceeds the maximum allowable variation.

BRIEF DESCRIPTION OF THE DRAWINGS

The invention will now be described, by way of example only, in reference to the drawings.

FIG. 1 is a block diagram showing a typical dual chamber pacemaker system arrangement.

FIG. 2 is a flow chart showing operation of a dual chamber pacing system according to the invention.

FIG. 3 is another flow chart showing operation of the dual chamber pacing system after detection of a sinus tachycardic rhythm.

FIG. 4 is still another flow chart showing operation of the dual chamber pacing system after detection of an arrhythmic rate.

DETAILED DESCRIPTION OF PREFERRED EMBODIMENTS

FIG. 1 schematically shows the structure of an implantable dual chamber pacemaker system 10 including a power unit 11 (i.e., a pulse generator) for applying stimulation pulses to two leads 12, 13 adapted to be implanted into two chambers of the patient's heart, typically the right atrium and the right ventricle.

Communication between pacemaker 10 and stimulation leads 12 and 13 may be bidirectional, in that leads 12 and 13 are preferably adapted to sense cardiac activity within the two heart chambers in question and convey respective sensing signals to the pacemaker 10. Sensing of cardiac activity may however be performed by other means, e.g., through separate electrodes.

Operation of pacemaker 10 is controlled by a control unit 14, preferably arranged to enable bidirectional communication with a programming unit/interface 15 located outside the patient's body. Unit/interface 15 is usually operated by a clinician in order to periodically check pacemaker operation and patient's conditions on the basis of telemetry data sent from pacemaker 10 to unit 15. Similarly, unit 15 is adapted to selectively modify the criteria of operation of pacemaker 10 by means of telemetry signals sent under the clinician's control from unit 15 towards unit 14 of the pacemaker.

All of the foregoing corresponds to principles and criteria which—per se—are well known in the art, thereby rendering a detailed description superfluous. In general, unit 14 of the pacing system of this invention can be programmed—in a manner known per se—to operate in any of the standard pacing modes of a dual-chamber pacemaker (e.g., DDD, DDDR, VDD, VDDR).

Referring to FIG. 2, a flow chart illustrating the automatic mode switching algorithm will now be described. This algorithm is executed in a loop, continuously providing the pacemaker with the capability of distinguishing between a pathologic arrhythmia and other conditions such as normal sinus tachycardia. A complete loop of the algorithm follows a cardiac cycle. This algorithm provides the pacing system with the capability of switching its mode of operation from a primary atrial tracking mode to an alternate atrial tracking mode if a pathologic arrhythmia is detected, as well as the capability of switching back to the primary mode once the pathological arrhythmia terminates.

At each cycle, the estimated atrial rate (EAR) is the sensed rate calculated limiting to a predetermined value the maximum amount by which it may change from the value of the atrial rate of the previous cycle. This allows any sinus rate to be correctly tracked, smoothing atrial rate variations related to physiologic intrinsic beat-to-beat variations.

The above mentioned predetermined value is set on the basis of the maximum physiological heart rate increase during exercise, considering that typically heart sinus rate at exercise increases exponentially with a half-time ranging from 10 to 45 seconds. See, in that respect, "Rate Adaptive Cardiac Pacing: Single and Dual Chamber" (C. P. Lau, Futura Publishing Company, Inc.; Mount Kisko, N.Y., 1993- p. 8).

The maximum tracking atrial rate (MTAR) is typically a programmable maximum rate value at which the pacing system tracks the intrinsic atrial rate when pacing the ventricles.

The Maximum Allowable Variation (MAV) is the maximum value at which the variation ($\Delta AR$) between the atrial rate (AR) and the EAR is not considered pathologic, determined as a function of the sympatho-vagal balance, expressed by heart rate variability (HRV).

The Minimum Tachy Detection Rate (MTDR) is the minimum absolute value under which atrial rate is never considered pathologic.

After start (step 100), with the system set to operate in a DDD mode (step 102) and a respective counter set to N=0 (step 104), the pacing system acquires an amplified P-wave signal from the atrium (step 106) and then determines (step 108) the atrial rate (AR). This is done by measuring the interval in milliseconds (ms) between the P-wave sensed during the current cardiac cycle and the P-wave sensed during the previous cardiac cycle, and then dividing the number 60,000 by the interval to produce the AR in beats per minute (bpm).

Then the atrial rate variation ΔAR is calculated (step 110) as the difference between the AR and the EAR of the previous cardiac cycle. Then the AR is compared, in step 112, with MTAR.

When the AR is below the MTAR (i.e., negative outcome of step 112), AR is compared with MTDR in step 114, and ΔAR is possibly compared with MAV in step 116. If either AR is below the MTDR or the ΔAR is below the MAV, the ventricular pacing rate PR is equal to the intrinsic AR and operation proceeds with step 118 to be described later.

When the AR exceeds the MTAR (i.e., positive outcome of step 112), the control system proceeds through a comparison step 120 to set the ventricular pacing rate to MTAR (step 122), leaving the pacing system to operate in demand mode by increasing by one the count of the captioned counter (step 124) and returning upstream of step 106.

If the AR exceeds the MTAR for more than a programmable number of cycles ($N_{IN}$), which corresponds to a negative outcome of step 120, then mode switch to VDI mode of operation occurs caused by the detection of a sinus tachycardic rhythm (step 126).

When the ΔAR exceeds the MAV (i.e., positive outcome of step 116), the control system proceeds through a comparison step 128 to limit the ventricular pacing rate to EAR+MAV (step 130), leaving the pacing system to operate in demand mode by increasing by one the count of the captioned counter (step 132) and returning upstream of step 106. If the ΔAR exceeds the MAV for more than a programmable number of cycles ($N_{IN}$), which corresponds to a negative outcome of step 128 then mode switch to VDI mode of operation occurs (step 134) caused by the detection of arrhythmic tachycardic rate.

In the case of a negative outcome of step 116, after step 118 (wherein the system calculates the EAR), operation proceeds with calculating the HRV (step 200) and the MAV as a function of the HRV (step 202) and the PR is set equal to the AR in step 204. Then another cycle operating in DDD mode begins by returning upstream of step 102.

FIG. 3 is a flow chart illustrating operation of the pacemaker when the detection of a sinus tachycardic rhythm have changed in step 126 the primary mode of operation (e.g., DDD or DDDR) to an alternate mode of operation (e.g., VDI or VDIR) which is asserted in step 136.

In step 138 the PR is set to MTAR value and two respective count indicia J and I are set to zero in steps 140 and 142, respectively. Then the control systems allows the pacing system to acquire an amplified P-wave signal from the atrium (step 144) and then determines the atrial rate (AR), which is measured in step 146.

This is done by measuring the interval in milliseconds between the P-wave sensed during the current cardiac cycle and the P-wave sensed during the previous cardiac cycle, and then dividing the number 60,000 by the interval to produce the AR in beats per minute (bpm).

The system then proceeds by comparing the AR with the MTAR in step 148. Depending on the outcome of step 148, the system evolves towards two further comparison steps 150, 152 where counting indicia J and I are compared with respective threshold values N and $N_{OUT}$.

More specifically, in the case of a positive outcome of step 148 (i.e., the AR is higher than the MTAR), count index I is forced to zero in step 154 and index J is increased by one to proceed to step 150. Alternatively, in the case of a negative outcome of step 148, count index I is increased by one in step 158 to proceed with comparison step 152.

In summary, when the AR remains above the MTAR for a predetermined number of cycles (N), the PR is determined by a fallback algorithm toward the basic rate (step 160). If the AR remains under the MTAR for a predetermined number of cycles (as defined by $N_{OUT}$), the pacemaker automatically changes its current mode of operation to the primary mode of operation (e.g., DDD or DDDR) in step 162. The negative outcome of step 150 (i.e., indicia J and I being still lower than N and $N_{OUT}$, respectively) simply returns the system upstream of step 144 after setting the PR to MTAR in step 164.

Step 165 is a step substantially similar to step 164 which is taken in the case of a negative outcome of step 152 to return upstream of step 144.

FIG. 4 is a flow chart illustrating operation of the pacemaker when the detection of a arrhythmic tachycardic rhythm has changed in step 134 the primary mode of operation (e.g., DDD or DDDR) to an alternate mode of operation (e.g., VDI or VDIR), which is asserted in step 166.

In step 168, the PR is set to EAR+MAV value and then, after setting count index I to zero in step 170, the control systems allows the pacing system to acquire an amplified P-wave signal from the atrium (step 172) and determine the atrial rate (AR). This is done in step 174 by measuring the interval in milliseconds between the P-wave sensed during the current cardiac cycle and the P-wave sensed during the previous cardiac cycle, and then dividing the number 60,000 by the interval to produce the AR in beats per minute (bpm). In subsequent step 176 the AR is compared with the quantity EAR+MAV. When the AR remains above the EAR+MAV (i.e., positive outcome of step 176), the count index I is forced to zero in step 178 and the PR is determined by a fallback algorithm toward the basic rate (step 180), the system then returning upstream of step 172.

In the case of a negative outcome of step 176, the count index I is increased by one in step 182 and the count index thus increased is compared in step 184 with a threshold value identified by $N_{OUT}$. A negative outcome of step 184 leads the system to proceed upstream of step 180. A positive outcome of step 184 leads the system to switch back to the primary mode of operation (step 186). In short, if the AR remains under the EAR+MAV for a predetermined number of cycle ($N_{OUT}$), the pacemaker changes automatically its current mode of operation to the primary mode of operation (e.g., DDD or DDDR).

Details and embodiments of the invention may vary without departing from the scope of the invention as defined by the claims.

What is claimed is:

1. An implantable heart-stimulation system, comprising:
   a first sensing element configured to sense atrial signals;
   a second sensing element configured to sense ventricular signals;
   a pulse generator configured to generate atrial and ventricular stimulating signals; and
   a control unit configured to determine for each cardiac cycle an atrial rate from the sensed atrial signals, to determine for each cardiac cycle a maximum allowable variation of the atrial rate as a function of sympatho-vagal balance, and to switch from an atrial tracking pacing mode to a non-atrial tracking pacing mode when a variation in the atrial rate between a first cardiac cycle and a second cardiac cycle exceeds the maximum allowable variation.

2. The system according to claim 1, wherein the sympatho-vagal balance is expressed by heart rate variability.

3. The system according to claim 2, wherein the heart rate variability is measured by means of an index.

4. The system according to claim 3, wherein the index is calculated as the number of atrial intervals, which in a predetermined time interval or number of beats differ from the preceding interval more than a predetermined quantity.

5. The system according to claim 4, wherein the number of beats is 100.

6. The system according to claim 4, wherein the time interval is one minute.

7. The system according to claim 4, wherein the predetermined quantity is 50 milliseconds.

8. The system according to claim 1, wherein the maximum allowable variation of the sensed atrial rate is a positive linear function of an index of the sympatho-vagal balance.

9. The system according to claim 1, wherein the control unit is configured to determine for each cardiac cycle an estimated atrial rate and wherein the control unit is configured to calculate the variation in the atrial rate as the difference between the sensed atrial rate of a present cardiac cycle and the estimated atrial rate of the previous cardiac cycle.

10. The system according to claim 9, wherein the estimated atrial rate is a moving average rate calculated at each cycle.

11. The system according to claim 1, wherein the control unit is programmable.

12. A method of controlling the pacing mode of a heart stimulation system implanted in a patient, the system including first and second sensors for sensing atrial and ventricular signals, a pulse generator for generating and providing atrial and ventricular stimulation pulses to the patient's heart and a control unit for controlling the pacing mode of the system, the method comprising:

determining in the control unit an atrial rate of the patient's heart from the sensed atrial signals;

determining in the control unit a maximum allowable variation of the atrial rate for each cardiac cycle as a function of sympatho-vagal balance; and switching from an atrial tracking pacing mode to a non-atrial tracking pacing mode when a variation in atrial rate from a first cardiac cycle to a second cardiac cycle exceeds the maximum allowable variation.

13. The method according to claim 12, wherein, in the step of determining the maximum allowable variation of the atrial rate, the sympatho-vagal balance is expressed by heart rate variability.

14. The method according to claim 13, wherein the heart rate variability is measured by means of an index.

15. The method according to claim 14, wherein the index is calculated as the number of atrial intervals, which in a predetermined time interval or number of beats differ from the preceding interval more than a predetermined quantity.

16. The method according to claim 15, wherein the number of beats is 100.

17. The method according to claim 15, wherein the time interval is one minute.

18. The method according to claim 15, wherein the predetermined quantity is 50 milliseconds.

19. The method according to claim 12, wherein, in the step of determining the maximum allowable variation of the atrial rate, the maximum allowable variation of the sensed atrial rate is a positive linear function of an index of the sympatho-vagal balance.

20. The method according to claim 12, further comprising calculating in the control unit an estimated atrial rate for each cardiac cycle and wherein the variation in atrial rate is calculated as the difference between the sensed atrial rate of a present cardiac cycle and the estimated atrial rate of the previous cardiac cycle.

21. The method according to claim 20, wherein the estimated atrial rate is a moving average rate calculated at each cycle.

22. The method according to claim 12, wherein the control unit is programmable.

* * * * *